(12) United States Patent
Edelmann et al.

(10) Patent No.: US 8,609,374 B2
(45) Date of Patent: Dec. 17, 2013

(54) CELL EXTRACT PROMOTED CLONING

(75) Inventors: Winfried Edelmann, Bronx, NY (US); Yongwei Zhang, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 13/526,930

(22) Filed: Jun. 19, 2012

(65) Prior Publication Data

US 2013/0045508 A1 Feb. 21, 2013

Related U.S. Application Data

(60) Provisional application No. 61/502,972, filed on Jun. 30, 2011.

(51) Int. Cl.
*C12P 19/34* (2006.01)
*C12P 21/06* (2006.01)
*C12N 15/64* (2006.01)

(52) U.S. Cl.
USPC ....... 435/91.1; 435/69.1; 435/91.2; 435/91.4; 435/91.5

(58) Field of Classification Search
None
See application file for complete search history.

(56) References Cited

U.S. PATENT DOCUMENTS

2006/0134739 A1* 6/2006 Chatterjee .................... 435/69.1

OTHER PUBLICATIONS

Li et al., "Harnessing homologous recombination in vitro to generate recombinant DNA via SLIC" 4(3) Nature Methods 251-256 (2007).*
Yu et al., "An efficient recombination system for chromosomoe engineering in *Escherichia coli*" 97(11) Proceedings of the National Academy of Sciences 5978-5983 (2000).*
Zhang et al., A new logic for DNA enginerring using recombination in *Escherichia coli* 20 Nature Genetics 123-128 (1998).*
Zhang Y et al., entitled "SLiCE: a novel bacterial cell extract-based DNA cloning method," Nucleic Acids Research, 2012, vol. 40, No. 8, e55, 10 pages & 4 Suppl pages, published online Jan. 12, 2012.

* cited by examiner

*Primary Examiner* — Anne Gussow
*Assistant Examiner* — Nancy J Leith
(74) *Attorney, Agent, or Firm* — Amster, Rothstein & Ebenstein LLP

(57) ABSTRACT

Methods are disclosed for assembling a plurality of double-stranded DNA fragments into DNA molecules in a single in vitro recombination reaction comprising contacting the plurality of double-stranded DNA fragments with a bacterial extract derived from a RecA deficient bacterial strain so as to assemble the plurality of DNA fragments into DNA molecules.

19 Claims, 3 Drawing Sheets

CELL EXTRACT PROMOTED CLONING

CROSS-REFERENCE TO RELATED APPLICATION

This application claims the benefit of U.S. Provisional Patent Application No. 61/502,972, filed on Jun. 30, 2011, the contents of which are herein incorporated by reference.

STATEMENT OF GOVERNMENT SUPPORT

This invention was made with government support under grant numbers CA76329 and CA93484 awarded by the National Institutes of Health. The government has certain rights in the invention.

BACKGROUND OF THE INVENTION

Throughout this application various publications are referred to in superscripts. Full citations for these references may be found at the end of the specification. The disclosures of these publications are hereby incorporated by reference in their entirety into the subject application to more fully describe the art to which the subject invention pertains.

The generation of recombinant deoxyribonucleic acid (DNA) molecules is an essential tool in modern molecular biology. The conventional DNA cloning strategies that have been used for several decades typically involve the use of type II restriction enzymes to generate appropriate DNA fragments, the modification of DNA ends to generate blunt or sticky ends and the ligation of the DNA fragments to generate plasmid or other type DNA vectors[1-3]. However, these procedures depend on the presence of appropriate restriction sites to generate both vector and insert molecules and often leave unwanted sequences at the junction sites. In addition, the restriction enzymes and modifying enzymes required for these manipulations are often expensive making these procedures costly especially in high throughput settings. The present invention addresses the need for a seamless and restriction site-independent cloning method.

SUMMARY OF THE INVENTION

The present invention provides methods of assembling a plurality of double-stranded DNA fragments into DNA molecules in a single in vitro recombination reaction comprising contacting in vitro the plurality of double-stranded DNA fragments with a bacterial extract derived from a RecA deficient bacterial strain so as to assemble the plurality of DNA fragments into DNA molecules, wherein each DNA fragment has a 3' end and a 5' end, and wherein fragments assemble with each other when the 5' end of one fragment has 20 bp to 52 bp that are homologous with the 3' end of another fragment.

DETAILED DESCRIPTION OF THE INVENTION

Figures 1A, 1B, 1C, 1D, 1E:
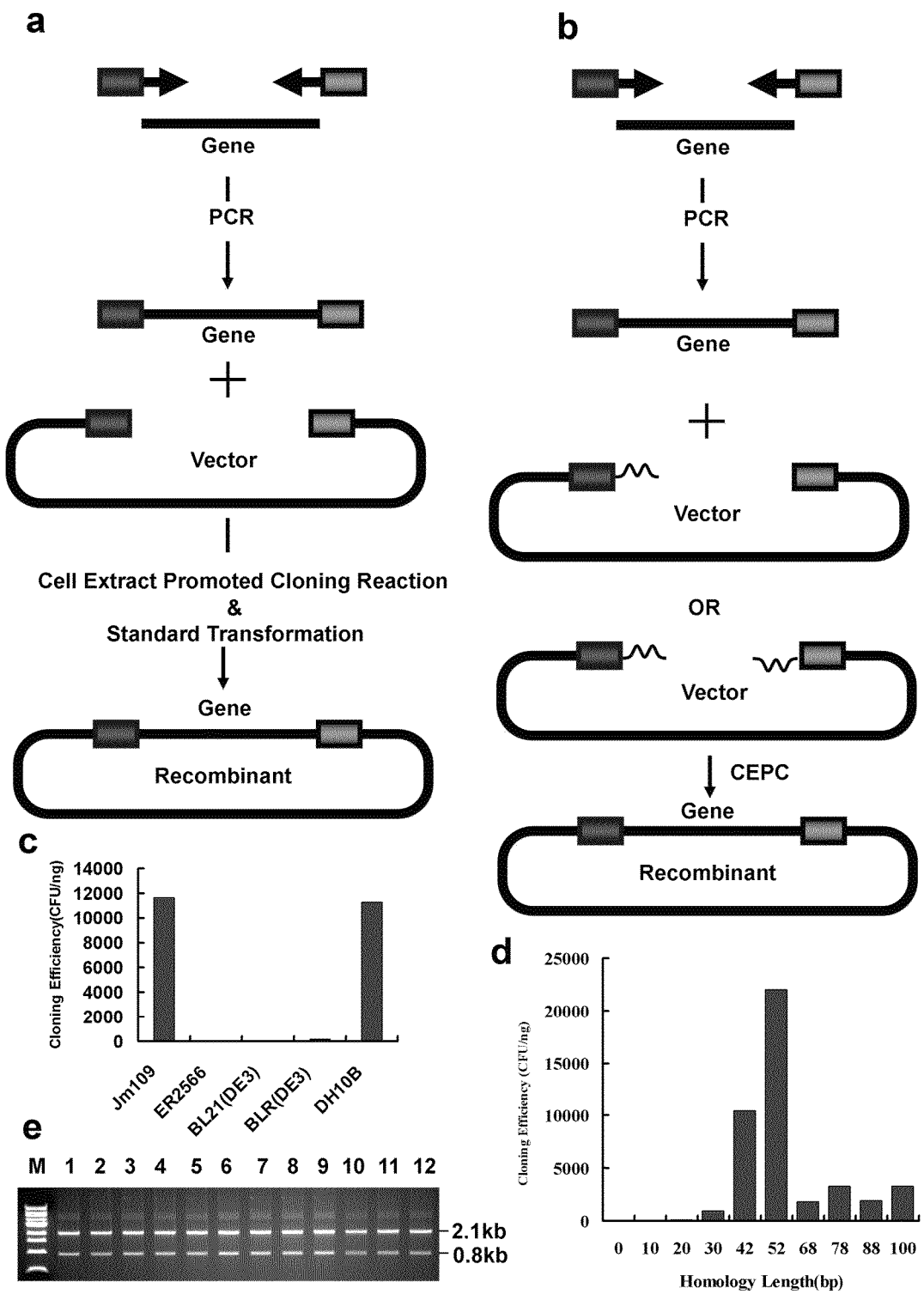
FIG. 1a-1e. Cell Extract Promoted Cloning. a) Outline of Cell Extract Promoted Cloning. b) Schematic illustrating authentic seamless CEPC cloning. c) Comparison of CEPC efficiency of E. coli K 12 strains. d) The influence of homology length on CEPC in DH10B extracts. e) BsaAI/SapI restriction analysis of the recombinants derived from CEPC cloning. Plasmid DNAs from twelve independent ampicillin-resistant blue colonies (lanes 1-12) were digested with BsaAI/SapI. The digestion products were separated on a 1% agarose gel and visualized after ethidium bromide staining. Recombinant plasmids contain one BsaAI site and one SapI site yielding diagnostic 2.1 kb and 0.8 kb restriction fragments.

The present invention provides a method of assembling a plurality of double-stranded DNA fragments into DNA molecules in a single in vitro recombination reaction comprising contacting in vitro the plurality of double-stranded DNA fragments with a bacterial extract derived from a RecA deficient bacterial strain so as to assemble the plurality of DNA fragments into DNA molecules, wherein each DNA fragment has a 3' end and a 5' end, and wherein fragments assemble with each other when the 5' end of one fragment has 20 bp to 52 bp that are homologous with the 3' end of another fragment. Preferably, 30 bp to 52 bp are homologous.

RecA is a bacterial protein involved in the repair and maintenance of DNA.

The bacteria can be, for example, a RecA deficient Escherichia coli strain, such as, for example, DH10B strain (Invitrogen) or JM109 strain (Promega).

The 3 prime (3') end of DNA has a free hydroxyl group at the 3' carbon of the sugar. The 5 prime (5') end has a phosphate group at the 5' carbon of the sugar. Two nucleotides on opposite complementary DNA strands that are connected via hydrogen bonds are called a base pair (bp); i.e., adenine (A) forms a base pair with thymine (T) and guanine (G) forms a base pair with cytosine (C). As used herein, sequences of base pairs are "homologous" if the sequences are identical.

The DNA fragments can comprise heterologous sequences of up to 1,000 bp adjacent to the homologous end of the fragment.

The in vitro recombination reaction can be performed without the prior use of a DNA restriction enzyme, a DNA modifying enzyme and/or a DNA ligase. DNA restriction enzymes recognize and cleave a specific short sequence (i.e., the restriction site) in DNA molecules. DNA ligase joins the 3' end of one nucleic acid strand with the 5' end of another. DNA modifying enzyme include, for example, Klenow and T4 DNA polymerase.

The DNA fragments can be produced, for example, by amplifying DNA using polymerase chain reaction (PCR). The DNA fragments can also be produced by digesting a plasmid vector or a bacterial artificial chromosome (BAC) with restriction enzymes.

The methods disclosed herein are suitable for assembly of chemically synthesized DNA fragments. The DNA fragments that are assembled can be chemically synthesized DNA fragments. The DNA can be or can contain complementary DNA (cDNA) synthesized from a messenger RNA (mRNA).

The efficiency of the method can be increased by modifying the bacteria prior to obtaining the bacterial extract. For example, redα, redβ and gam genes[e.g., 4-6, 9-10] can be introduced into the genome of the RecA deficient bacteria from which the bacterial extract is derived. Bacteria can be modified, for example, to constitutively express the λ phage redβ and gam genes under the control of the EM7 and Tn5 promoters, respectively, and also the redα gene under the control of an arabinose-inducible pBAD promoter (araC-pBAD).

The recombinant DNA molecules that are assembled can be transformed into host bacteria to in order to amplify the DNA molecules using standard procedures known in the art.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

In order to circumvent limitations of earlier cloning procedure, a seamless and restriction site-independent cloning method was developed that is based on in vitro recombination between short regions of homologies (20 bp-52 bp) in bacterial cell extracts termed Cell Extract Promoted Cloning (CEPC), and more recently Seamless Ligation Cloning Extract (SLiCE).

CEPC allows for efficient restriction site-independent cloning of DNA fragments generated by restriction digestion or PCR amplification into linearized vectors. In addition, CEPC does not require the use of enzymes for the modification of vector and insert end sequences (such as Klenow or T4 DNA polymerase) or ligases. The CEPC method can be used for virtually any type of cloning approach including the simple subcloning of PCR or restriction fragments, the generation of tagged expression vectors, the construction of more complex vectors such as gene targeting vectors or the directional subcloning of larger DNA fragments from more complex vectors such as bacterial artificial chromosomes (BACs).

The CEPC method is based on bacterial extracts that can be derived from a variety of common RecA⁻ E. coli laboratory strains such as DH10B and JM109. These strains can also be further optimized by simple genetic modifications to improve CEPC cloning efficiencies and capabilities making CEPC highly versatile. For example, a DH10B-derived strain, termed PPY, was established that was engineered to contain an optimized λ prophage Red recombination system[4-6]. Extracts derived from this strain provide the highest cloning efficiencies thus far; it can be used for all cloning approaches that are routinely used in the laboratory. The CEPC method overcomes many problems related to conventional cloning procedures and provides a highly cost effective approach for the generation of recombinant DNA molecules in a seamless and restriction site-independent manner.

Materials and Methods

Bacteria Strains:

The following laboratory E. coli strains were used: DH10B (Invitrogen), JM109 (Promega), BL21(DE3) (Invitrogen), BLR(DE3) (Novagen) and ER2566(NEB). The DH10B derived E. coli strain PPY was constructed by Suicide Plasmid Based Genome Modification[21] using plasmid pGT1 (PPY genotype: F⁻ endA1 recA1 galE15 ga/K16 nupG rpsL ΔlacX74 Φ80lacZ ΔM15 araD139 Δ(ara,leu)7697 mcrA Δ(mrr-hsdRMS-mcrBC) cynX:: [araC pBAD-redα EM7-redβ Tn5-gam]λ⁻). The competent cells used for transformation of CEPC generated recombination products were ElectroMAX DH10B™ cells and MAX Efficiency® DH10B™ competent cells (Invitrogen).

Plasmids:

The plasmid pBL was constructed by insertion of a 70 bp chemically synthesized multiple cloning site into the 2.5 kb PCR-generated plasmid backbone of pBluescript II KS(+) (Stratagene) and deletion of the LacZ ORF by conventional cloning. The plasmid pBL-DL was constructed by insertion of a 1.0 kb PCR fragment from pGEM®-luc (Promega) into the NotI/SalI sites of pBL by CEPC. The suicide plasmid pGT1 was constructed by CEPC-mediated insertion of a 830 bp PCR amplified fragment spanning the 3' region of the E. coli DH10B cynX gene and an araC-pBAD-redα/EM7-redβ/Tn5-gam expression cassette isolated from plasmid pBAD24[22] and lambda phage DNA (NEB) into the SmaI site of plasmid pEL04[23]. pGT1 also contains a temperature-sensitive replicon and a chloramphenicol selection marker.

Preparation of CEPC Extracts:

E. coli strains were grown at 37° C. in 100 ml 2×YT medium until they reached $OD_{600}$≈5.3 ($OD_{600}$ readings were calculated by diluting the sample to enable photometric measurement in the linear range between 0.1 and 0.5 $OD_{600}$). PPY was subsequently incubated for 2 h in 2×YT medium containing 0.2% L-arabinose to express λ prophage protein Exo. The cells were harvested by centrifugation at 5000 g for 20 minutes at 4° C. The cells from 96 ml of original culture (wet weight≈0.92 g) were washed 1 time with 200 ml dd$H_2O$ and resuspended in 1.2 ml CelLytic™ B Cell Lysis Reagent (Sigma). The resuspended cells were incubated at room temperature for 10 minutes to allow lysis to occur. The cell lysates were centrifuged at 20000 g for 2 minutes to pellet the insoluble material. The resulting supernatants were carefully removed from the cell debris and mixed with equal volume of 100% glycerol and stored at −20° C. For long term storage the cells were stored at −80° C. with or without the addition of glycerol.

CEPC Reaction and Transformation:

The vectors used for CEPC were linearized by restriction digestion or PCR amplification. The cloning inserts were PCR amplified using primers containing 5'-end homologies to the vector or to other inserts for co-assembly. Vector or insert DNAs that was generated by PCR amplification using plasmid DNA as templates were treated with DpnI prior to purification to remove residual plasmid template DNA. The linearized vectors and PCR inserts were subjected to gel electrophoresis and purified using the QIAEX II gel extraction kit. For CEPC cloning of BAC DNA, the restriction digested BAC DNA was purified by phenol/chloroform extraction.

The standard CEPC reaction mix contained the following ingredients: 50-200 ng linear vector, appropriate amount of insert DNA in a 1:1 to 10:1 molar ratio of insert to vector, 1 µl 10×CEPC buffer (500 mM Tris-HCl (pH7.5 at 25° C.), 100 mM $MgCl_2$, 10 mM ATP, 10 mM DTT), 1 µl CEPC extract and dd$H_2$O to a total volume of 10 µl. The CEPC reaction was incubated at 37° C. for 1 hour and subsequently 1 µl of the CEPC reaction was electroporated into 20 µl ElectroMAX DH10B™ cells or chemically transformed into 100 µl MAX Efficiency® DH10B™ competent cells. The transformed cells were plated on ampicillin/Xgal agar plates or agar plates containing appropriate antibiotics.

Results

Comparison of E. coli K12 Strains for CEPC:

CEPC is a cloning method that is based on in vitro recombination in bacterial extract. CEPC is a simple and efficient procedure with the entire process consisting of 3 steps (FIG. 1a): 1) The preparation of linear vector and insert fragments containing short end homologies introduced by PCR with primers having appropriate 5' extension sequences; 2) the CEPC in vitro reaction and 3) the standard transformation of recombination products into suitable host bacteria. The CEPC reaction includes linearized vector and insert DNA fragments containing homology at their 5' and 3' ends, CEPC extract from bacteria, 10×CEPC buffer and dd$H_2$O in a total volume of 10 µl. The exact details for CEPC extract preparation, CEPC buffer and the CEPC reaction are described in the methods section.

To determine the most efficient bacterial strains for CEPC, five standard laboratory E. coli K12 strains were tested including DH10B, JM109, ER2566, BL21 (DE3) and BLR (DE3). The main criteria for their selection included their genetic status with regard to the RecA homologous recombination protein and the presence of restriction systems that could interfere with the stability of exogenous DNA (Table 4).

To determine the suitability of extracts derived from these strains for CEPC, a simple cloning strategy was devised. A plasmid vector termed pBL was linearized by restriction digestion and incubated together with a 500 bp PCR amplified LacZ in the different bacterial extracts. To facilitate recombination the LacZ fragment contained 42 bp end sequences that were homologous to the 5' and 3' end sequences of pBL. According to the experimental design positive recombinant clones could be identified by blue/white selection after transformation and growth of bacteria on ampicillin/Xgal agar plates.

This analysis showed that extracts from the two RecA⁻ strains DH10B and JM109 yielded the highest cloning efficiencies, indicating that CEPC is facilitated by a RecA independent mechanism (FIG. 1c).

Due to the high cloning efficiency, cell extract from the DH10B strain was further used for the analysis of CEPC. Using the pBL-LacZ cloning strategy described above, the influence of several parameters on CEPC cloning efficiency was tested including the lengths of end homologies, the vector/insert ratio and the overall DNA concentration. To determine the effect of end homology length on CEPC, homologies ranging from 0 to 100 bp (as counted from the 3' ends of the vector) were tested (FIG. 1d). This analysis showed that inserts without end homology or 10 bp end homology did not yield any recombinant colonies. In contrast, 20 bp of end homology already yielded an appreciable number of recombinant colonies at a cloning efficiency of 80 CFU/ng of vector, while 30 bp of end homology provided very robust cloning efficiencies (920 CFU/ng of vector). A further increase in end homology length resulted in even higher cloning efficiencies with an end homology length of 52 bp providing the highest efficiency (21965 CFU/ng of vector). However, in contrast to in vivo homologous recombination cloning, the cloning efficiency dropped significantly when the end homology length was further increased (FIG. 1d), indicating that CEPC promotes in vitro recombination by a different pathway. Next, CEPC was performed with varying vector/insert molar ratios at a vector concentration of 10 ng/µl and 42 bp of end homology. These studies showed that vector/insert ratios of 1:1, 1:2, 1:6 and 1:10 yielded 1,335, 2,330, 11,120 and 12,120 CFU/ng of vector, respectively, demonstrating that excessive insert ratios could yield higher cloning efficiencies. Compared to the standard vector concentration of 10 ng/µl, CEPC using low concentrations of vector (1 ng/µl) and a vector/insert at ratio of 1:1 led to a 200-fold decrease in cloning efficiency which is likely due to the instability of vector and insert DNA at these low concentration in the CEPC reaction mix. Control reactions that contained the same vector/insert combinations with increasing end homologies but without CEPC extract did not yield any recombinant colonies.

Besides promoting recombination between homologous sequences at the ends of vector and inserts, CEPC is also capable of facilitating recombination between DNA fragments that contain flanking heterologous sequences and of deleting the extra flanking sequences to generate precise junctions at the recombination sites. This feature of CEPC provides a highly useful cloning tool, especially in those cases where the absence of suitable restriction sites in a vector prevent the seamless cloning of an insert fragment into a desired vector region (termed "authentic seamless" cloning activity, see FIG. 1b). To test this feature, DH10B CEPC reactions were performed with vector pBL-DL that was designed to provide heterologous flanking sequences at the cloning sites. pBL-DL was linearized with appropriate restriction enzymes to generate flanking heterologous sequences on one side (319 bp, 738 bp and 998 bp) or on both sides (45 bp plus 23 bp and 319 bp plus 738 bp) and was together with a LacZ fragment of 500 bp with 42 bp of end homologies (FIG. 1b) subjected to CEPC followed by blue/white selection. The results showed that DH10B CEPC can efficiently remove 45 bp plus 23 bp of flanking heterologous sequences but it cannot facilitate DNA cloning with longer flanking heterologous sequences of 319 bp, 738 bp, 998 bp on one side or 319 bp plus 738 bp on both sides (Table 5).

Generation of a Modified DH10B Strain for the Optimization of CEPC:

In vivo homologous recombination in E. coli can be facilitated by three different recombination pathways: The RecA dependent pathway, a RecA independent pathway of unknown nature and a RecA independent pathway that utilizes prophage Red/ET recombination systems[4-11]. The studies above indicate that a RecA independent pathway catalyzes CEPC. To optimize CEPC and acquire even more efficient strains as a source for cell extracts, the DH10B genome was modified using a suicide plasmid based strategy to insert an optimized λ prophage Red recombination system into the bacterial genome. Specifically, the genome of DH10B bacteria were modified to constitutively express the λ phage redβ and gam genes under the control of the EM7 and Tn5 promoters, respectively, and also the red$\alpha$ gene under the control of an arabinose-inducible pBAD promoter (araC-pBAD). The modified DH10B strain was termed PPY and tested for CEPC. Extracts derived from PPY bacteria yielded significantly higher cloning efficiencies and a more robust authentic seamless cloning activity than the DH10B extracts (see below) and were used in the following series of experiments for the analysis of optimized CEPC capabilities.

Efficiency and Fidelity of PPY CEPC:

The first series of experiments investigated the efficiency and fidelity of the improved PPY CEPC extract. First, the influence of end homology length was examined on PPY CEPC mediated cloning in more detail. Using the same pBL-LacZ cloning strategy end homologies varying from 0 bp to 100 bp were examined (Table 1). Vector and insert fragments with no end homology or a short homology of 10 bp did not yield any recombinant colonies. Similar to DH10B CEPC without the Red system, the minimum length of homology required for efficient cloning was 20 bp, however, the PPY CEPC extracts yielded an dramatic increase in the number of blue recombinant colonies (34,500 CFU vs. 920 CFU per ng of vector, PPY CEPC vs. DH10B CEPC) with a more than 200-fold stimulation over white non-recombinant background colonies. Similar to DH10B CEPC cloning, the cloning efficiency for PPY CEPC increased with homology length in a range up to 52 bp but dropped significantly when the end homologies were further increased (see Table 1).

PPY CEPC-mediated cloning was also performed using another vector/insert combination (p3XFLAG-CMV-7.1 vector (Invitrogen) and a 800 bp PCR insert with end homologies ranging from 0 bp to 42 bp). These studies yielded similar results (data not shown).

The recombinant colonies derived from PPY CEPC cloning were further analyzed by colony PCR, restriction digestion and DNA sequencing analyses. More than 300 blue colonies were screened using colony PCR (data not shown) and some of the colonies were verified by restriction digestion (see FIG. 1e). All of the analyzed clones contained the correct insert. The vector/insert junctions of 30 recombinant clones were sequenced and all of the clones contained the correct cloning junctions indicating that CEPC fuses vector and insert in a precise manner. The small number of white background colonies that were observed in these test experiments could be traced back to spurious amounts of undigested pBL vector during linearization.

Next, the fidelity of PPY CEPC was examined without prior selection of positive recombinant clones. These studies were conducted using a NotI/XbaI linearized 5.2 kb plasmid vector and a 1.4 kb PCR amplified insert with 30 bp of end homologies. The entire insert and the junction regions of 20 positive recombinants were sequenced. 18 recombinants contained completely correct sequences and 2 recombinants presented one mutant nucleotide located in the PCR insert, which is consistent with the error rate of the DNA polymerase that was used for PCR amplification (Fastart Fidelity PCR system, Roche) at $2.4 \times 10^{-6}$ per bp per cycle and 30 cycle amplification. The error rate and location of mutations indicate that these mutations were caused by PCR amplification of inserts and that CEPC did not introduce further mutations.

The effect of various molar ratios of vector and insert and the overall DNA concentration on PPY CEPC were then examined. The results were again similar to DH10B CEPC mediated cloning. PPY CEPC with pBL-LacZ vector/inserts at molar ratios of 1:1, 1:2, 1:6 and 1:10 with 20 bp end homologies yielded 19240, 27320, 34500 and 65350 CFU/ng of vector, respectively, showing that addition of excessive insert yields only moderately higher cloning efficiencies for PPY CEPC. PPY CEPC at a low concentration of vector and insert (1 ng/µl) at a vector/insert ratio of 1:1 resulted in a 10-fold reduced cloning efficiency.

To determine the effect of insert length on PPY CEPC cloning efficiencies, vectors ranging in size from 2.0 kb to 15 kb and containing inserts ranging from 80 bp to 21 kb in size were assembled. The cloning of larger fragments by CEPC occurred at robust but somewhat reduced efficiencies (data not shown). For example, the assembly of an 11.0 kb recombinant plasmid containing an 8.0 kb insert was achieved at a cloning efficiency of 140 CFU/ng of vector. The restriction analysis of 24 clones revealed that 22 contained the expected recombinant plasmid.

CEPC-mediated cloning has been used to generate more than 100 recombinant plasmids employing various cloning strategies and many different vector/insert combinations. The results indicate that CEPC can be considered a universal cloning method for the generation of recombinant DNA at high fidelity. Furthermore, the nature of vector and insert ends such as blunt ends or 3' or 5' sequence overhangs did not influence CEPC efficiency or accuracy. However, the use of vectors with complementary 5' or 3' overhanging ends for CEPC increased the formation of empty vector background colonies, which is probably due to annealing of the single stranded ends in the bacterial extracts or in the transformed host cells.

Authentic Seamless Cloning Activity of PPY CEPC:

The authentic seamless cloning activity of PPY CEPC was examined using the same pBL-DL-LacZ cloning strategy as for DH10B CEPC with flanking heterologous sequences at one side (2 bp, 319 bp, 738 bp and 998 bp) or on both sides (45 bp plus 23 bp and 319 bp plus 738 bp) and with various end homologies.

In comparison to DH10B extracts, PPY extracts presented a much stronger seamless activity, which can remarkably increase the efficiency of DNA cloning especially with shorter flanking heterologies (45 bp plus 23 bp on both sides; 7,600 CFU vs. 1,265 CFU per ng of vector, PPY extract vs. DH10B extract). In addition, PPY CEPC can efficiently remove longer flanking heterologous sequences of up to 998 bp on one side or up to 319 bp plus 738 bp on both sides (Table 2). In general, vectors with shorter flanking sequences or flanking sequences on only one side yielded higher cloning efficiencies compared to vectors with longer and/or double-sided flanking heterologous sequences (Table 2). Similar to CEPC cloning without flanking heterologous sequences, longer end homologies between vector and insert resulted in higher cloning efficiencies (Table 2).

Figures 2A, 2B, 2C, 2D, 2E:
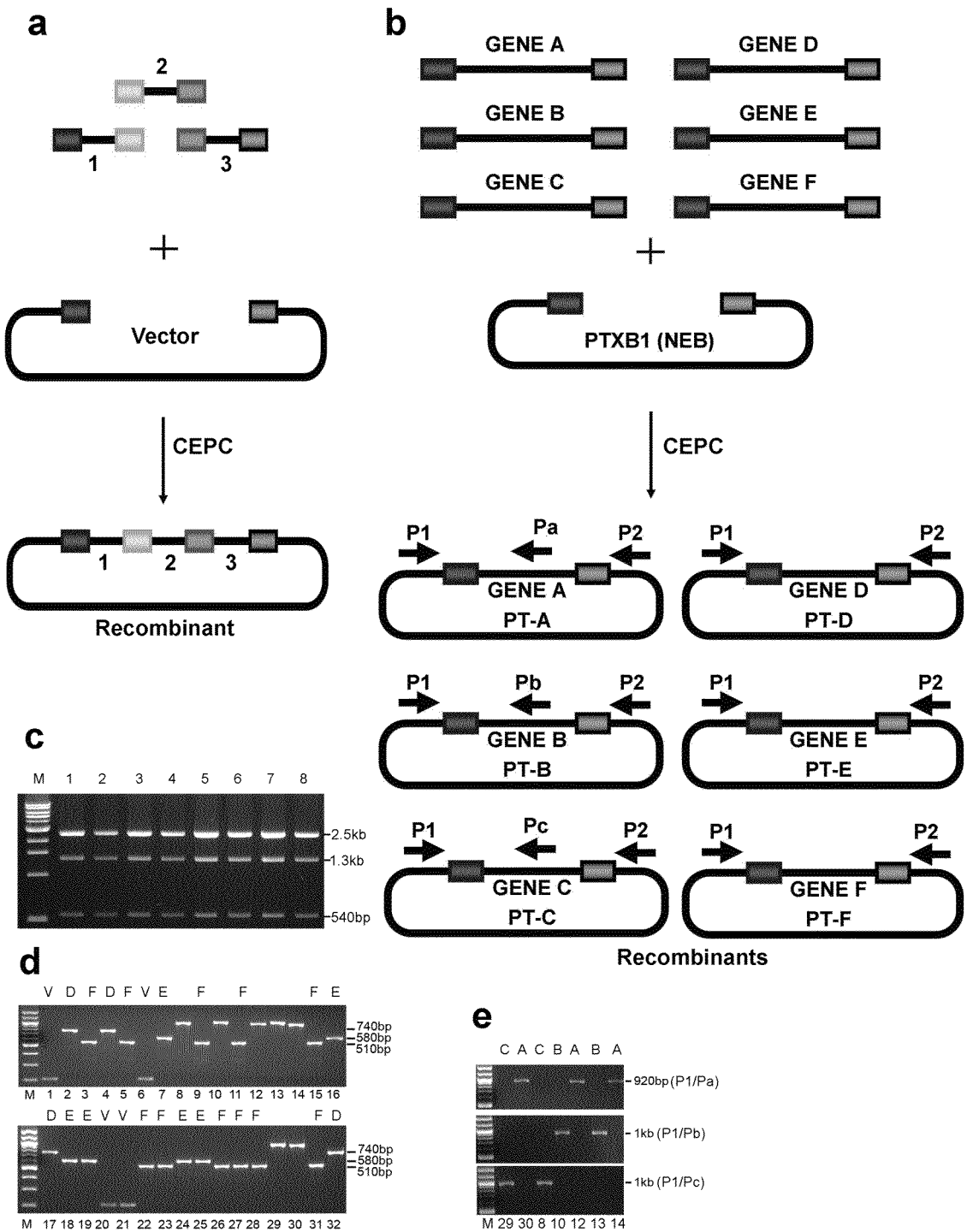
FIG. 2a-2e. CEPC Cloning With Multiple Fragments. a) Schematic illustrating multiple-way CEPC cloning. A 3-way cloning approach is shown. b) Schematic illustrating batch CEPC cloning. Six PCR inserts with 30 bp homology and plasmid vector PTXB1 (NdeI/SapI) were subjected to batch CEPC cloning. P1, P2, Pa, Pb and Pc refer to the primers for colony PCR screening. c) BsaAI/XmnI restriction analysis of the recombinants derived from 7-way CEPC cloning. Plasmid DNAs from eight independent ampicillin-resistant colonies (lanes 1-8) were digested with BsaAI/XmnI. Recombinants contain one BsaAI site and one XmnI site located within the vector and one BsaAI site located in the insert yielding diagnostic 2.5 kb, 1.3 kb and 540 bp restriction fragments. d) PCR screening of recombinants derived from batch CEPC cloning of six different inserts. 32 independent colonies (lanes 1-32) were subjected to PCR analysis with primer pair P1/P2. Recombinant plasmids PT-A, PT-B and PT-C all yielded PCR products of about 1.0 kb (lanes labeled with asteriscs). Recombinant plasmids PT-D, PT-E and PT-F yielded PCR products of 740 bp, 586 bp and 510 bp, respectively (lanes labeled D, E and F). Non-recombinant vector pTXB1 yielded a PCR product of 210 bp using primer pair P1/P2 (lanes labeled V). e) To identify PT-A, PT-B and PT-C recombinants were further analyzed using primer pairs P1/Pa, P1/Pb and P1/Pc. The PCR products of PT-A using primer pair P1/Pa, PT-B using primer pair P1/Pb and PT-C using primer pair P1/Pc were 920 bp, 1.0 kb and 1.0 kb respectively (shown in lanes labeled A, B and C, respectively).

CEPC Cloning with Multiple Fragments:

The high cloning efficiency and fidelity of PPY CEPC suggested it might be possible to generate more complex recombinant plasmids using multiple inserts in a single cloning reaction. To test this idea two different CEPC strategies were designed for the cloning of multiple insert fragments. In the first strategy, an attempt was made to clone multiple inserts into one vector in one CEPC reaction to generate a single recombinant DNA molecule derived from multiple fragments and was termed multiple-way CEPC cloning (FIG. 2a). The second strategy was designed to clone several different inserts carrying the same end homology into a vector in one CEPC reaction in parallel. This strategy creates multiple different recombinant DNA molecules and was termed CEPC batch cloning (FIG. 2b).

To examine the potential CEPC for of multiple-way cloning, 3-way, 4-way and 7-way multiple CEPC cloning was performed using the pBL vector and 3 different sets of PCR amplified inserts with 42 bp of end homology that can assemble into a single 1.9 kb DNA fragment expressing LacZ activity (FIG. 2c). The studies showed that PPY CEPC mediated 3-way, 4-way and 7-way multiple cloning occurred at significant efficiencies (6,610, 4,080 and 3,260 CFU/ng of vector, respectively) and high accuracies (percentage number of correct clones to total number of clones: 88%, 96% and 90%, respectively). DNA sequencing analysis showed that all of the multiple fragments were precisely joined by CEPC mediated multiple-way cloning.

Multiple-way CEPC cloning was examined using other vectors and inserts. A 3-way CEPC using a 4.7 kb vector (p3XFLAG-CMV-7.1, Invitrogen) and two 250 bp inserts with 24 bp of end homologies produced about 500 CFU/ng of vector with a 10-fold simulation over non-recombinant background colonies. Another 3-way experiment assembled a 3.0 kb vector and two 2.6 kb and 2.5 kb inserts using 42 bp of end homology with 80% accuracy and a cloning efficiency of 60 CFU/ng of vector. To determine the ability of multiple-way CEPC cloning to assemble highly complex vector/insert combinations, a 4-way cloning strategy (42 bp end homology, 2.5 kb of vector, inserts of 500 bp, 1.4 kb and 2.5 kb) and a 7-way strategy with shorter end homology (24 bp homology, 2.5 kb of vector and six inserts totaling 2.0 kb) were performed. For both multiple-way cloning strategies the cloning efficiencies were reduced but still provided at least 20 CFU/10 ng of vector.

For CEPC batch cloning, two sets of experiments were performed. Six PCR inserts varying from 300 bp to 1.0 kb with 30 bp of end homology were mixed together with a linearized 6.7 kb prokaryotic expression vector (PTXB1, NEB) were incubated in PPY CEPC extract (FIG. 2b). About 340 CFU/ng of vector were obtained. The analysis of 32 colonies showed that all six possible recombinant plasmids/insert combinations were obtained (FIG. 2d and FIG. 2e). Another experiment using a 4.7 kb mammalian expression vector (p3XFLAG-CMV-7.1, Invitrogen) and 3 inserts of 1.0 kb, 1.5 kb and 2.5 kb with 24 bp homology yielded similar results (data not shown).

Figure 3A:
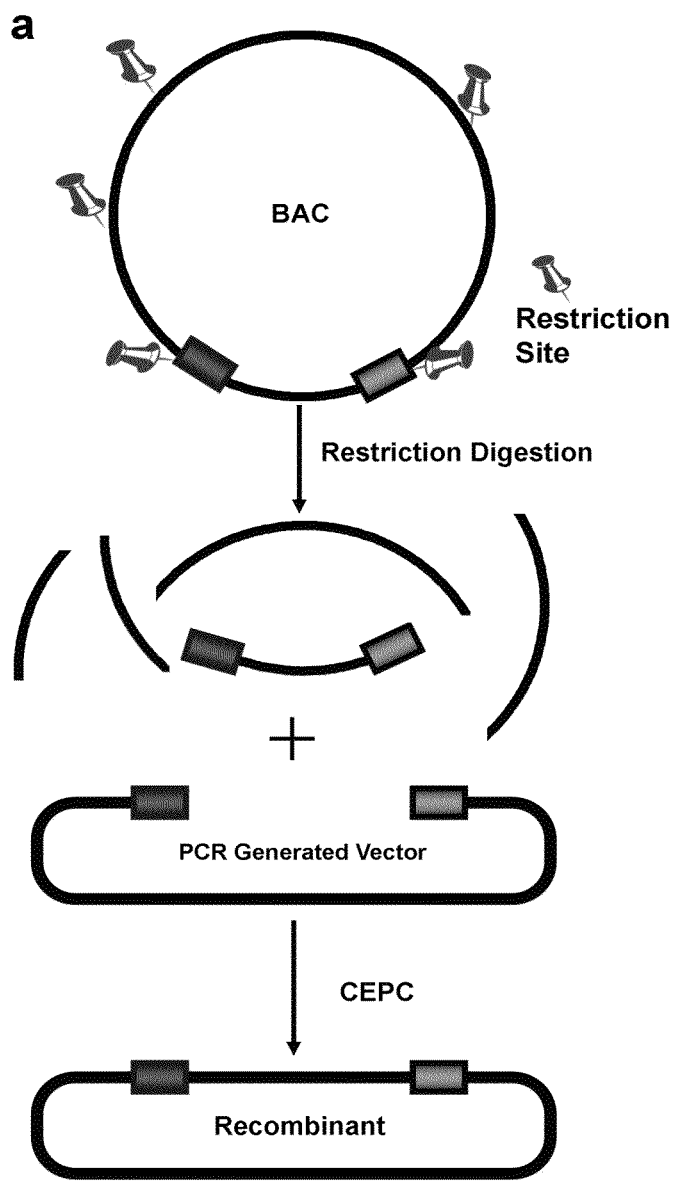
FIG. 3a-3c. BAC CEPC Cloning. a) Schematic illustrating BAC CEPC cloning. b) XmnI/XhoI restriction analysis of recombinants derived from CEPC cloning of a 8.7 kb BglII BAC fragment. Plasmid DNAs from six independent ampicillin-resistant colonies (lanes 1-6) were digested with XmnI and XhoI. Recombinants contain one XmnI site within the vector and one XhoI site within the insert yielding diagnostic 7.2 kb and 4.0 kb restriction fragments. c) BamHI/BglII restriction analysis of recombinants derived from CEPC cloning of a 12.2 kb EcoRV BAC fragment. Plasmid DNAs from nine independent ampicillin-resistant colonies (lanes 1-9) were digested with BamHI and BglII. Recombinants contain one BglI site within the vector and two BamHI sites in the insert yielding diagnostic 5.9 kb, 4.9 kb and 3.9 kb restriction fragments.
Figure 3B:
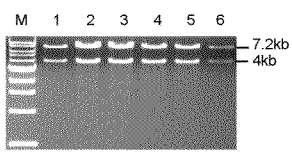
Figure 3C:
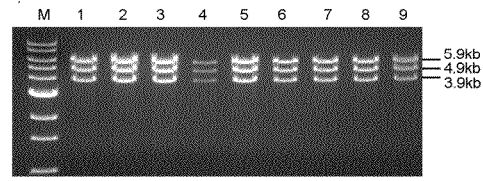

CEPC Cloning of Genomic Fragments from BAC Clones:

It is often challenging to subclone a genomic DNA fragment from larger DNA vectors such as BACs into a plasmid vector. Due to the high cloning efficiency of PPY CEPC, it was tested whether CEPC could also facilitate this type of cloning. A CEPC cloning strategy was designed to subclone individual genomic DNA fragments from BAC vectors (FIG. 3a). Specifically, BAC DNA isolated from clone RP23-303G13 (CHORI), 165 kb in size and containing 66 BglII and 19 EcoRV restriction sites, was digested with either BglII or EcoRV to generate a complex pool of DNA fragments. The digested BAC DNA was phenol/chloroform purified and subjected to PPY CEPC cloning with PCR-generated pBluescript derived vectors that contained end homologies to different BglII or EcoRV BAC restriction fragments. CEPC cloning was attempted of several BglII BAC fragments of different sizes (830 bp, 3.7 kb, 6.7 kb, 8.7 kb and 14 kb) with 42 bp or 52 bp of end homology. In addition, CEPC cloning was also performed for several EcoRV BAC fragments of larger sizes (5.3 kb, 6.3 kb, 12.2 kb and 21 kb) (Table 3). In all cases, recombinant clones were obtained carrying the different BAC fragments with high or acceptable cloning efficiencies (see Table 3 and FIG. 3b,c), indicating that CEPC cloning is an effective strategy for the directional subcloning of small or large BAC genomic fragments.

TABLE 1

Influence of End Homology Length on PPY CEPC Cloning

| End Homology Length (bp) | Cloning Efficiency | |
|---|---|---|
| | Blue Colonies | White Colonies |
| Vector Only | 0 | <50 |
| 0 | 0 | <50 |
| 10 | 0 | <50 |
| 20 | 34,500 | <50 |
| 30 | 124,000 | <50 |
| 42 | 632,000 | <50 |
| 50 | 766,000 | <50 |
| 68 | 162,000 | <50 |
| 78 | 119,250 | <50 |
| 88 | 68,000 | <50 |
| 100 | 32,500 | <50 |

Cloning efficiencies using different lengths of end homologies are given as colony forming units (CFU) per nanogram of vector. The 2.5 kb vector pBL was linearized by NotI/SalI digestion and the 500-700 bp LacZ fragments were prepared by PCR. Experiments were performed using 10 ng/µl of vector and the corresponding amount of insert DNA at a 1:6 molar ratio of vector:insert. The blue colonies contain recombinant plasmid and the white colonies contain non-recombinant vector background.

TABLE 2

Authentic Seamless PPY CEPC Cloning

| Homology Length (bp) | Vector Flanking Heterology Length (bp) | | Vector Length (bp) | Cloning Efficiency | |
|---|---|---|---|---|---|
| | Side 1 | Side 2 | | Blue Colonies | White Colonies |
| 20 | 2 | 0 | 2500 | 10,000 | 40 |
| 42 | 319 | 0 | 2803 | 2270 | 5 |
| 30 | 319 | 0 | 2803 | 1250 | 25 |
| 42 | 738 | 0 | 3222 | 1232 | 190 |
| 30 | 738 | 0 | 3222 | 432 | 126 |
| 42 | 998 | 0 | 3482 | 570 | 35 |
| 42 | 45 | 23 | 2552 | 7600 | 1810 |
| 30 | 45 | 23 | 2552 | 1288 | 760 |
| 20 | 45 | 23 | 2552 | 710 | 485 |
| 42 | 319 | 738 | 3541 | 5 | 0.1 |

Cloning efficiencies are given as colony forming units (CFU) per nanogram of vector. Vectors containing different end heterologies were derived from plasmid pBL-DL by digesting with various restriction enzymes. LacZ inserts of 500 bp size containing the indicated end homologies were generated by PCR. The experiments were performed using 10-40 ng/µl vector DNA and the corresponding amount of insert DNA at a 1:6 molar ratio of vector:insert in a 10 µl reaction volume. The blue colonies contain recombinant plasmid and the white colonies contain non-recombinant vector background.

TABLE 3

BAC CEPC Cloning

| End Homology Length (bp) | Restriction Enzyme | Insert Length (kb) | Cloning Efficiency | Cloning Accuracy |
|---|---|---|---|---|
| 42 | BglII | 0.83 | 97 | 75% |
| 42 | BglII | 3.7 | 37 | 44% |
| 42 | BglII | 6.7 | 171 | 47% |
| 52 | BglII | 8.7 | 52 | 12% |
| 52 | BglII | 14 | 42 | 14% |
| 42 | EcoRV | 5.3 | 197 | 62% |
| 42 | EcoRV | 6.3 | 277 | 76% |
| 52 | EcoRV | 12.2 | 130 | 66% |
| 52 | EcoRV | 21 | 19 | 53% |

Cloning efficiencies are given as colony forming units (CFU) per nanogram of vector. Cloning accuracies are given as the percentage of correct clones among total number of amp[r] clones. pBluescript II KS+ (Stratagene) was used as template to PCR amplify linear vectors containing end homologies corresponding to various BglII or EcoRV restriction fragments in BAC clone RP23-303G13. Vector DNA (10-20 ng/ul) and total BglII or EcoRV digested BAC DNA (1 ug/ul) were subjected to PPY CEPC cloning.

TABLE 4

E. coli K12 strains analyzed for CEPC

| E. coli K12 Strains | Genotype |
|---|---|
| DH10B | F⁻ endA1 recA1 galE15 galK16 nupG rpsL ΔlacX74 Φ80lacZΔM15 araD139 Δ(ara, leu)7697 mcrA Δ(mrr-hsdRMS-mcrBC) λ⁻ |
| JM109 | endA1 glnV44 thi-1 relA1 gyrA96 recA1 mcrB⁺Δ(lac-proAB) e14- [F' traD36 proAB⁺ lacI$^q$ lacZΔM15] hsdR17($r_K^-$ $m_K^+$) |
| BL21(DE3) | F⁻ ompT gal dcm lon hsdS$_B$($r_B^-$ $m_B^-$) (DE3) |
| BLR(DE3) | F⁻ ompT hsdS$_B$($r_B^-$ $m_B^-$) gal dcm (DE3) Δ(srl-recA)306::Tn10 (Tet$^R$) |
| ER2566 | F⁻ fhuA2 [lon] ompT lacZ::T7 gene1 gal sulA11 Δ(mcrC-mrr)114::IS10 R(mcr-73::miniTn10-Tet$^S$)2 R(zgb-210::Tn10)(Tet$^S$) endA1 [dcm] λ⁻ |
| PPY | F⁻ endA1 recA1 galE15 galK16 nupG rpsL ΔlacX74 Φ80lacZΔM15 araD139 Δ(ara, leu)7697 mcrA Δ(mrr-hsdRMS-mcrBC) cynX:: [araC pBAD- redα EM7-redβ Tn5-gam] λ⁻ |

TABLE 5

Authentic Seamless DH10B CEPC cloning

| Homology Length | Vector Flanking Heterology Length (bp) | | Vector Length | Cloning Efficiency | |
|---|---|---|---|---|---|
| | Side 1 | Side 2 | | Blue Colonies | White Colonies |
| 42 bp | 45 | 23 | 2552 bp | 1265 | 890 |
| 42 bp | 319 | 0 | 2803 bp | 0 | 80 |
| 42 bp | 738 | 0 | 3222 bp | 0 | 190 |
| 42 bp | 998 | 0 | 3482 bp | 0 | 60 |
| 42 bp | 319 | 738 | 3541 bp | 0 | 50 |

Cloning efficiencies are given as colony forming units (CFU) per nanogram of vector. Vectors containing different end heterologies were derived from plasmid pBL-DL by digesting with various restriction enzymes. LacZ inserts of 500 bp size containing 42 bp of end homologies were generated by PCR. The experiments were performed using 10-40 ng/μl vector DNA and the corresponding amount of insert DNA at a 1:6 molar ratio of vector:insert in a 10 μl reaction volume. The blue colonies contain recombinant plasmid and the white colonies contain non-recombinant vector background.

Discussion

The observation that bacterial cell extracts can efficiently recombine DNA molecules using short end homologies was a serendipitous discovery. After initial characterization and further optimization, a novel restriction site-independent and seamless cloning method was established that was termed CEPC. Simple cell extracts from two RecA deficient laboratory strains, JM109 and DH10B, were shown to efficiently recombine vector and insert DNA containing short end homologies. In addition, these strains can be further optimized for CEPC by simple genetic modification. In this study the genes of the λ prophage Red recombination system and the gam gene were introduced into the DH10B genome to generate a new bacterial strain termed PPY. This strain currently provides the highest cloning efficiencies and facilitates CEPC in a wide variety of cloning applications.

Bacterial extracts have been shown to efficiently catalyze RecA-dependent homologous recombination[12]. However, CEPC-mediated cloning is working most efficiently in RecA-deficient extracts indicating that it utilizes a different recombination pathway. The existence of a RecA-independent recombination pathway in E. coli that mediates exchange at short homologies has been proposed[7]. It was suggested that this RecA-independent recombination mechanism involves the generation of short 5' and 3'-tailed strands that anneal to homologous molecules[8] and that E. coli single-strand exonucleases such as RecJ, ExoVII, ExoI and ExoX could degrade these tails and abort the exchange reaction. Consistent with this notion, the RecA-independent recombination was stimulated in the absence of these single-strand exonucleases. It is likely that CEPC-mediated cloning involves the activities of exonucleases or helicases for the generation of single-strand tails at the ends of vectors and inserts, single-strand binding proteins for the stabilization of these single-strand overhangs and possibly other factors that protect 5' and 3' tails from degradation and facilitate their annealing. Consistent with this idea, although CEPC mediated recombination is efficient in the absence of the prophage Red/ET recombination systems, the introduction of the redα, redβ and gam genes, which facilitate similar transactions at single stranded DNA ends, into DH10B bacteria greatly enhanced CEPC mediated cloning.

Although PPY CEPC shares some features with the recently developed in vivo recombineering methods[13-16], it is different in several aspects. Recombineering methods provide useful tools for DNA modification and depend on homologous recombination that is mediated by the λ-prophage encoded Red recombination system in vivo in bacterial cells. In contrast, CEPC is an in vitro recombination method facilitated by bacterial cell extracts. The Red recombination system is not required for CEPC but can be used to further increase the cloning efficiencies of CEPC. In addition, the main application of recombineering is the modification of large DNA molecules such as BACs or bacterial genomes, while CEPC can be used as a general cloning method for the generation of recombinant plasmids.

Compared to conventional ligation dependent cloning methods including the cloning of DNA fragments with sticky or blunt ends generated by restriction digestion or the TA cloning of PCR fragments, CEPC has several important advantages: 1) It is a time and labor saving method that consists of a one-hour/one-tube reaction followed by standard transformation of host bacteria. 2) It does not require any prior treatment of end sequences. 3) CEPC can be used to directionally clone one or more fragments into any vector with high efficiency and fidelity. 4) It promotes seamless cloning without leaving any unwanted sequences at the cloning junctions.

The ability to seamlessly join DNA fragments is an important feature of CEPC and greatly aides in the generation of precisely engineered vectors that are essential for many molecular biology studies such as promoter analyses, protein structure-function studies, protein tagging and engineering as well as more complex vectors such as gene targeting vectors used for genome manipulation.

In addition to CEPC, several other in vitro homologous recombination based cloning systems have recently been described, SLIC[17,18] and six commercially available cloning systems including IN-FUSION® PCR Cloning[19,20] (Clontech), Cold Fusion Cloning Kit (SBI), Fast Seamless Cloning Kit (Dogene), CLONEEZ® Kit (Genescript), and GENE-ART® Seamless Cloning and Assembly Kit (Invitrogen). SLIC uses the 3'-5' exonuclease activity of T4 DNA polymerase to generate ssDNA overhangs in insert and vector which are required for the fusion of vector and insert fragments by single strand annealing with or without the addition of RecA. IN-FUSION® PCR Cloning promotes PCR cloning by the IN-FUSION® enzyme, a poxvirus DNA polymerase with 3'-5 exonuclease activity. The mechanisms or enzymatic activities involved in the other commercial cloning systems have not been disclosed by the suppliers, but it is likely that they utilize processes that are similar to that of SLIC and IN-FUSION® PCR Cloning.

In comparison to CEPC, SLIC is more labor intensive and requires optimization. Vector and insert fragments for SLIC need to be treated individually with T4 DNA polymerase and the treatment duration is not always constant but depends on the homology length[18].

The efficient authentic seamless cloning activity is one of the most important features of CEPC as it allows the recombining of vector and inserts in vitro even in the presence of flanking heterologous sequences of up to 938 bp on one side or 319 bp plus 738 bp on both sides. This property decreases the sequence dependence of end cloning by CEPC and greatly extends its usefulness for many applications. SLIC also has seamless cloning activity; however, it is limited to flanking heterologies of only up to 20 bp. There are no reports that IN-FUSION® PCR Cloning (Clontech) or any of the other commercially available in vitro cloning systems any such activity. Furthermore, CEPC is the only known in vitro recombination based method for the directional subcloning of genomic BAC fragments into plasmid vectors. At present it is not clear if the other in vitro cloning systems can be used for this application.

In summary, CEPC is an easy, efficient and inexpensive cloning method that allows the generation of recombinant plasmid vectors in a seamless and precise fashion. It requires the generation of simple bacterial cell extracts from readily available lab strains and does not require the use of restriction enzymes or DNA end modification enzymes such as Klenow or T4 DNA polymerase. In addition, the joining of vector and insert fragments by DNA ligase is not required. CEPC is a highly versatile method.

REFERENCES

1. Smith, H. O. & Wilcox, K. W. A restriction enzyme from *Hemophilus influenzae*. I. Purification and general properties. *J. Mol. Biol.* 51:379-391 (1970).
2. Danna, K. & Nathans, D. Specific cleavage of simian virus 40 DNA by restriction endonuclease of *Hemophilus influenzae*. *Proc. Natl. Acad. Sci. USA* 68, 2913-2917 (1971).
3. Cohen, S. N., Chang, A. C., Boyer, H. W. & Helling, R. B. Construction of biologically functional bacterial plasmids in vitro. *Proc. Natl. Acad. Sci. USA* 70:3240-3244 (1973).
4. Little J W. An exonuclease induced by bacteriophage lambda. II. Nature of the enzymatic reaction. *J Biol Chem.* 242(4): 679-86 (1967).
5. Radding C M, Carter D M. The role of exonuclease and beta protein of phage lambda in genetic recombination. 3. Binding to deoxyribonucleic acid. *J Biol Chem.* 246(8): 2513-8 (1971).
6. Carter D M, Radding C M. The role of exonuclease and beta protein of phage lambda in genetic recombination. II. Substrate specificity and the mode of action of lambda exonuclease. *J Biol Chem.* 246(8):2502-12 (1971).
7. Lovett, S. T., Hurley, R. L., Sutera, V. A., Jr., Aubuchon, R. H., and Lebedeva, M. A. Crossing over between regions of limited homology in *Escherichia coli*. RecA-dependent and RecA-independent pathways. *Genetics* 160:851-859 (2002).
8. Dutra, B. E., Sutera, V. A., and Lovett, S. T. RecA-independent recombination is efficient but limited by exonucleases. *Proc Natl Acad Sci USA* 104:216-221 (2007).
9. Muyrers J P, Zhang Y, Buchholz F, Stewart A F. RecE/RecT and Redalpha/Redbeta initiate double-stranded break repair by specifically interacting with their respective partners. *Genes Dev.* 14:1971-82 (2000).
10. Kuzminov A. Recombinational repair of DNA damage in *Escherichia coli* and bacteriophage lambda. *Microbiol Mol Biol Rev.* 63:751-813 (2002).
11. Persky N S, Lovett S T. Mechanisms of recombination: lessons from *E. coli*. *Crit Rev Biochem Mol Biol.* 43:347-70 (2008).
12. Kolodner R. Genetic recombination of bacterial plasmid DNA: electron microscopic analysis of in vitro intramolecular recombination. *Proc Natl Acad Sci USA.* 77:4847-5 (1980).
13. Murphy, K. C. Use of bacteriophage λ recombination functions to promote gene replacement in *Escherichia coli*. *J. Bacteriol.* 180:2063-2071 (1998).
14. Zhang, Y., Buchholz, F., Muyrers, J. P. & Stewart, A. F. A new logic for DNA engineering using recombination in *Escherichia coli*. *Nature Genet.* 20:123-128 (1998).
15. Yu, D. et al. An efficient recombination system for chromosome engineering in *Escherichia coli*. *Proc. Natl Acad. Sci. USA* 97:5978-5983 (2000).
16. Muyrers, J. P., Zhang, Y., Testa, G. & Stewart, A. F. Rapid modification of bacterial artificial chromosomes by ET-recombination. *Nucleic Acids Res.* 27:1555-1557 (1999).
17. Aslanidis, C. and de Jong, P. J. Ligation-independent cloning of PCR products (LIC-PCR). *Nucleic Acids Res.* 18:6069-6074 (1990).
18. Li M Z, Elledge S J. Harnessing homologous recombination in vitro to generate recombinant DNA via SLIC. *Nat Methods.* 4:251-6 (2007).
19. Clontechniques. BD In-Fusion cloning kit. Precise, directional cloning of PCR products without restriction enzymes. *CLONTECHniques* XVII:10-11 (2002).
20. Hamilton, M. D., A. A. Nuara, D. B. Gammon, R. M. Buller and D. H. Evans. Duplex strand joining reactions catalyzed by vaccinia virus DNA polymerase. *Nucleic Acids Research* 35:143-151 (2007).
21. Fehér T, Karcagi I, Gyorfy Z, Umenhoffer K, Csörgo B, Pósfai G. Scarless. Engineering of the *Escherichia coli* genome. *Methods Mol. Biol.* 416:251-9 (2008).
22. Guzman L M, et al. Tight regulation, modulation, and high-level expression by vectors containing the arabinose PBAD promoter. *J. Bacteriol.* 177: 4121-4130 (1995).
23. Lee, E. C., Yu, D., Martinez de Velasco, J., Tessarollo, L., Swing, D. A., Court, D. L, Jenkins, N. A., and Copeland, N. G. A highly efficient *Escherichia coli*-based chromosome engineering system adapted for recombinogenic targeting and subcloning of BAC DNA. *Genomics.* 73:56-65 (2001).

What is claimed is:

1. A method of assembling a plurality of double-stranded DNA fragments into DNA molecules in a single in vitro recombination reaction comprising contacting in vitro the plurality of double-stranded DNA fragments with a bacterial extract from a RecA deficient bacterial strain so as to assemble the plurality of DNA fragments into DNA molecules, wherein each DNA fragment has a 3' end and a 5' end, wherein fragments assemble with each other when the 5' end of one fragment has 20 bp to 100 bp that are homologous with the 3' end of another fragment, wherein heterologous sequences, when present, of up to 1000 bp that flank the homologous region are removed prior to assembling the DNA fragments into DNA molecules, and wherein the in vitro recombination reaction is performed without the addition of any of an exogenous DNA restriction enzyme, an exogenous DNA modifying enzyme, or an exogenous DNA ligase.

2. The method of claim 1, wherein fragments assemble with each other when the 5' end of one fragment has 30 bp to 52 bp that are homologous with the 3' end of another fragment.

3. The method of claim 1, wherein the DNA fragments comprise heterologous sequences of up to 1,000 bp adjacent to the homologous end of the fragment.

4. The method of claim 1, wherein the DNA fragments are produced by digesting a plasmid vector or a bacterial artificial chromosome (BAC) with restriction enzymes.

5. The method of claim 1, wherein the DNA fragments are produced by amplifying DNA using polymerase chain reaction (PCR).

6. The method of claim 1, wherein redα, redβ and gam genes are introduced into the genome of the RecA deficient bacteria prior to obtaining the bacterial extract.

7. The method of claim 1, wherein the bacteria are a RecA deficient *Escherichia coli* strain.

8. The method of claim 1, which comprises transforming the assembled recombinant DNA molecules into host bacteria to amplify the DNA molecules.

9. The method of claim 1, wherein the DNA fragments that are assembled are chemically synthesized DNA fragments.

10. The method of claim 1, wherein fragments assemble with each other when the 5' end of one fragment has 20 bp to 52 bp that are homologous with the 3' end of another fragment.

11. The method of claim 1, wherein the DNA fragments are produced by amplifying DNA.

12. A method of assembling a plurality of double-stranded DNA fragments into DNA molecules in a single in vitro recombination reaction comprising contacting in vitro the plurality of double-stranded DNA fragments with a bacterial extract from a RecA deficient bacterial strain so as to assemble the plurality of DNA fragments into DNA molecules, wherein each DNA fragment has a 3' end and a 5' end, and wherein fragments assemble with each other when the 5' end of one fragment has 20 bp to 100 bp that are homologous with the 3' end of another fragment, and wherein the DNA fragments are assembled into DNA molecules without the use of an exogenous DNA polymerase.

13. The method of claim 12, wherein the exogenous DNA polymerase is T4 DNA polymerase.

14. A method of assembling a plurality of double-stranded DNA fragments into DNA molecules in a single in vitro recombination reaction comprising contacting in vitro the plurality of double-stranded DNA fragments with a bacterial extract from a RecA deficient bacterial strain so as to assemble the plurality of DNA fragments into DNA molecules, wherein each DNA fragment has a 3' end and a 5' end, and wherein fragments assemble with each other when the 5' end of one fragment has 20 bp to 100 bp that are homologous with the 3' end of another fragment, and wherein more than 34,500 colony forming units are obtained per nanogram of DNA.

15. The method of claim 14, wherein more than 68,000 colony forming units are obtained per nanogram of DNA.

16. The method of claim 14, wherein more than 124,000 colony forming units are obtained per nanogram of DNA.

17. The method of claim 14, wherein more than 162,000 colony forming units are obtained per nanogram of DNA.

18. The method of claim 14, wherein more than 632,000 colony forming units are obtained per nanogram of DNA.

19. The method of claim 14, wherein redα, redβ and gam genes are introduced into the genome of the RecA deficient bacteria prior to obtaining the bacterial extract.

\* \* \* \* \*